United States Patent [19]
Han et al.

[11] Patent Number: 6,011,162
[45] Date of Patent: Jan. 4, 2000

[54] EPOXIDATION PROCESS USING IMPROVED HETEROGENEOUS CATALYST COMPOSITION

[75] Inventors: Yuan-Zhang Han, West Chester; Kevin M. Carroll, Havertown; Edrick Morales; Robert G. Gastinger, both of West Chester, all of Pa.

[73] Assignee: ARCO Chemical Technology, L.P., Greenville, Del.

[21] Appl. No.: 09/060,375

[22] Filed: Apr. 15, 1998

Related U.S. Application Data

[63] Continuation-in-part of application No. 08/900,794, Jul. 25, 1997, abandoned, which is a continuation-in-part of application No. 08/951,105, May 5, 1997, abandoned.

[51] Int. Cl.[7] .................................................. C07D 301/19
[52] U.S. Cl. .............................................................. 549/529
[58] Field of Search ............................................. 549/529

[56] References Cited

U.S. PATENT DOCUMENTS

| | | | |
|---|---|---|---|
| 3,166,542 | 1/1965 | Orzechowski et al. | 260/93.7 |
| 3,220,959 | 11/1965 | Orzechowski | 252/441 |
| 3,274,120 | 9/1966 | Aftandilian | 252/432 |
| 3,285,898 | 11/1966 | MacKenzie et al. | 260/92.3 |
| 3,923,843 | 12/1975 | Wulff | 260/318.5 |
| 4,367,342 | 1/1983 | Wulff et al. | 549/529 |
| 4,416,992 | 11/1983 | Arena | 435/176 |
| 4,876,372 | 10/1989 | Nakaishi et al. | 549/529 |
| 4,968,842 | 11/1990 | Padovan et al. | 564/253 |

FOREIGN PATENT DOCUMENTS

| | | |
|---|---|---|
| 0 345 856 | 5/1989 | European Pat. Off. . |
| 0 734 764 | 3/1996 | European Pat. Off. . |
| 0 792 859 A2 | 2/1997 | European Pat. Off. . |
| 527 908 | 1/1977 | Japan . |
| 1332526 | 1/1970 | United Kingdom . |
| 94/23834 | of 1994 | WIPO . |
| 96/09117 | 3/1996 | WIPO . |

OTHER PUBLICATIONS

Castillo et al., *J. Catalysis*, 161, pp. 524–529 (1996).
Fraile et al., *J. Chem. Soc. Chem. Commun.*, pp. 539–540 (1995).
Cativiela et al., *Tetrahedron*, 49, pp. 4073–4084 (1993).
Castillo et al., *J. Mater. Chem.*, 4(6) pp. 903–906 (1994).
Wauthoz et al., *Applied Catalysis*, 69, pp. 149–167 (1991).
Munoz–Paez et al., *Preparation of Catalysts V*, Poncelet et al. Eds., pp. 620–636 (1991).

*Primary Examiner*—Alan L. Rotman
*Assistant Examiner*—Raymond Covington
*Attorney, Agent, or Firm*—Stephen D. Harper

[57] ABSTRACT

Highly active and selective epoxidation catalysts are prepared by combining silica or the like with a non-oxygenated hydrocarbon solution of titanium halide, removing solvent, calcining at an elevated temperature (preferably, in a substantially oxygen-free atmosphere), and, optionally, reacting with water and silylating. The resulting materials are useful heterogeneous catalysts for transforming olefins to epoxides using organic hydroperoxides.

34 Claims, No Drawings

6,011,162

EPOXIDATION PROCESS USING IMPROVED HETEROGENEOUS CATALYST COMPOSITION

This is a continuation-in-part of Ser. No. 08/900,794, filed Jul. 25, 1997, which is a continuation-in-part of Ser. No. 08/851,105, filed May 5, 1997, each abandoned.

FIELD OF THE INVENTION

This invention relates to an improved epoxidation process wherein a titanium-containing catalyst composition is used. The catalyst composition is obtained by carrying out a liquid phase impregnation of a siliceous solid with a titanium halide such as titanium tetrachloride in a hydrocarbon solvent followed by calcination. Optionally, the catalyst is also reacted with water and/or a silylating agent. Catalyst performance is enhanced by performing the calcination at a high temperature (preferably, at least 700° C.) in the substantial absence of oxygen.

BACKGROUND OF THE INVENTION

Many different methods for the preparation of epoxides have been developed. One such method involves the epoxidation of an olefin in a liquid phase reaction using an organic hydroperoxide as the oxidizing agent and certain solubilized transition metal compounds as catalyst. The early work in the field concluded that optimum epoxidation rates and selectivity to epoxide generally are obtained using metallic catalysts which are soluble in an organic reaction medium.

A distinct disadvantage of an epoxidation process which utilizes a soluble metallic compound as catalyst is the difficulty associated with recovering the catalyst for reuse in subsequent runs. When the other components of an epoxidation reaction mixture (typically, epoxide, unreacted olefin, solvent, unreacted hydroperoxide, and the alcohol derived from the reacted hydroperoxide) are relatively volatile, these components may be separated from the soluble non-volatile catalyst by distillation and the catalyst recovered in the form of a bottoms stream. A problem associated with such a method, however, is that the bottoms stream may tend to accumulate certain heavy substances such as acids and polymers which may have a deleterious effect on epoxide selectivity or olefin conversion when the stream is reused. The catalyst may also have a tendency to precipitate from solution if the bottoms stream is overly concentrated; recycle of a relatively large bottoms stream may thus be required, which will detrimentally affect the productivity of the epoxidation process. It would therefore be highly desirable to develop an insoluble (heterogeneous) epoxidation catalyst which has high activity and selectivity and which may be readily recovered in active form from an epoxidation reaction mixture by filtration or similar separation techniques or which may be utilized in the form of a fixed bed or the like.

U.S. Pat. No. 4,367,342 discloses an olefin epoxidation process wherein an olefin is contacted with an organic hydroperoxide in the presence of an insoluble catalyst comprised of an inorganic oxygen compound of titanium. Such catalysts are further described in British Pat. No. 1,332,527 and U.S. Pat. Nos. 4,021,454, 3,829,392 and 3,923,843. Unfortunately, catalysts prepared in accordance with the procedures described in these references have less than optimum activity and selectivity. Incorporation of relatively high levels of titanium into catalysts of this type, in an attempt to improve catalyst activity, has also been challenging.

Consequently, it would be highly desirable to develop alternative methods of synthesizing heterogeneous titanium-containing catalysts which avoid the shortcomings of prior art procedures and reliably and conveniently provide materials having higher activity and selectivity in olefin epoxidation reactions.

British Patent No. 1,332,527 teaches a process for preparing an improved silica-titania catalyst characterized by impregnating an inorganic siliceous solid with a substantially non-aqueous solution of a titanium compound in an oxygen-substituted hydrocarbon solvent, removing solvent from the impregnated siliceous solid, and thereafter calcining the impregnated siliceous solid. Suitable solvents for this purpose are limited to oxa and/or oxo-substituted hydrocarbons which are liquid at ambient conditions and comprise generally from 1 to 12 carbon atoms. Such solvents include alcohols, ketones, ethers and esters. According to the patent, the reason why silica-titania catalyst produced by a process where an oxygen-substituted hydrocarbon impregnation solvent is used has improved properties compared to similar catalysts prepared by other methods is that such catalyst has a more uniform, non-agglomerated content of titanium dioxide.

A later-filed patent application (EP 345,856) discloses the preparation of epoxidation catalysts which are alleged to be more active than the analogous catalysts obtained by previously known procedures. EP 345,856 teaches impregnation of silica with a gaseous stream of titanium tetrachloride, followed by calcination, hydrolysis, and, optionally, silylation. In a comparative example, a catalyst prepared by silica impregnation with a solution of tetra isopropyl orthotitanate, complexed with acetyl acetone in isopropanol as solvent, was found to be 4.5 times less active than the catalyst prepared by vapor phase impregnation with titanium tetrachloride. The implication of this disclosure is that it is not possible to attain similar catalytic activity, while maintaining high epoxide selectivity, using a liquid phase rather than vapor phase impregnation process.

EP 734,764 teaches an improvement to the liquid phase impregnation process disclosed in British Pat. No. 1,323,527 wherein after impregnating silica with a solution of a titanium compound in an oxygen-containing organic solvent and removing the impregnation solvent the catalyst is washed with a washing solvent and then calcined. Preferably, the washing solvent is an alcohol. Washing prior to calcination is taught to be necessary in order to obtain a catalyst which is excellent both in activity and selectivity although examination of the comparative examples included in EP 734,764 indicates that only very modest improvement in catalyst performance is actually achieved using this procedure. Another practical disadvantage of this procedure is that large volumes of waste solvent are generated which must be either disposed of or recycled after purification. Such disposal or purification will substantially increase the cost of producing the catalyst. Another disadvantage is that it is difficult to achieve high levels of titanium incorporation, since washing tends to remove substantial amounts of titanium with this effect being even more pronounced using large quantities of the titanium reagent relative to the silica. Moreover, this procedure does not permit precise control of the final titanium content of the catalyst.

We have now discovered an effective, convenient method of producing catalyst compositions having epoxidation activity and selectivity at least comparable to catalysts obtained by the techniques taught in EP 345,856.

SUMMARY OF THE INVENTION

The invention provides an olefin epoxidation process, the catalyst composition used therein being obtained by a method comprising the steps of:

(a) impregnating an inorganic siliceous solid with a solution of a titanium halide in a non-oxygenated hydrocarbon solvent to form an impregnated siliceous solid;

(b) calcining the impregnated siliceous solid; said method being characterized by the substantial exclusion of water until at least after step (a) is completed.

Optionally, the catalyst preparation method comprises the additional steps of heating the catalyst in the presence of water (which may be performed at the same time as calcination) and/or treating the catalyst with a silylating agent. The epoxidation activity of the catalyst may be significantly improved by carrying out the calcination step at a relatively high temperature (e.g., 500° C. to 1000° C.) in the substantial absence of oxygen. The harmful effects of having oxygen present during calcination may, however, be overcome by introducing a reducing gas such as carbon monoxide into the calcination atmosphere.

DETAILED DESCRIPTION OF THE INVENTION

The epoxidation process of the invention utilizes a titanium-containing heterogeneous catalyst prepared by a particular method, which has unexpectedly been found to give materials having superior epoxidation performance as compared to the materials made using other liquid phase impregnation methods. The catalyst preparation method is characterized by impregnating an inorganic siliceous solid with a solution of titanium halide in a non-oxygenated hydrocarbon solvent. Suitable solvents for this purpose are those hydrocarbons which do not contain oxygen atoms, are liquid at ambient temperatures, and are capable of solubilizing the titanium halide. Generally speaking, it will be desirable to select hydrocarbon solvents wherein titanium halide concentrations of at least 0.5 percent by weight at 25° C. can be achieved. The hydrocarbon solvent should preferably be relatively volatile so that it may be readily removed from the inorganic siliceous solid following impregnation. Solvents having normal boiling points of from 25° C. to 150° C. thus may advantageously be utilized. Particularly preferred classes of hydrocarbons include, but are not limited to, $C_5$–$C_{12}$ aliphatic hydrocarbons (straight chain, branched, or cyclic), $C_6$–$C_{12}$ aromatic hydrocarbons (including alkyl-substituted aromatic hydrocarbons), $C_1$–$C_{10}$ halogenated aliphatic hydrocarbons, and $C_6$–$C_{10}$ halogenated aromatic hydrocarbons. Most preferably, the solvent does not contain elements other than carbon, hydrogen, and (optionally) halogen. If halogen is present in the solvent, it is preferably chloride.

Mixtures of non-oxygenated hydrocarbons may be used, if so desired. Preferably, the solvent used for impregnation purposes is essentially free of water (i.e., anhydrous). While oxygen-containing hydrocarbons such as alcohols, ethers, esters, ketones and the like could be present in admixture with the required non-oxygenated hydrocarbon, in one desirable embodiment of the invention only non-oxygenated hydrocarbon is present as a solvent during impregnation. Examples of suitable hydrocarbon solvents include n-pentane, n-hexane, n-heptane, n-octane, n-nonane, n-decane, neohexane, cyclohexane, cyclopentane, 2-methyl butane, methyl pentanes, methyl cyclohexane, dimethyl pentanes, methyl hexanes, dimethyl hexanes, methyl heptanes, trimethyl pentanes, benzene, toluene, xylenes, cumene, ethylbenzene, t-butyl benzene, methylene chloride, chloroform, carbon tetrachloride, ethyl chloride, dichloroethanes, tetrachloroethanes, chlorobenzene, dichlorobenzenes, trichloro-benzenes, benzyl chloride, chlorotoluenes, and the like and isomers thereof.

Unlike the procedure described in Example I of U.S. Pat. No. 4,021,454, wherein water is added to a mixture of titanium tetrachloride and silica in n-heptane, the process of this invention in preferred embodiments is characterized by the substantial exclusion of water until at least after impregnation is completed (i.e., after removal of the impregnation solvent) and preferably until after calcination. "Substantial exclusion" in the context of this invention means that water is not deliberately added or introduced or, if deliberately added or introduced, is removed prior to introduction of titanium halide (which will tend to react with water and interfere with the desired interaction of the titanium halide with the surface of the inorganic siliceous solid). The use of reagents and starting materials having water present at the trace levels normally and customarily found in such substances when sold on a commercial scale is within the scope of the present invention. Preferably, less than 500 ppm water (more preferably, less than 100 ppm water) is present in the non-oxygenated hydrocarbon. As will be subsequently described in more detail, it is highly desirable to dry the inorganic siliceous solid thoroughly prior to use.

Suitable titanium halides include titanium compounds having at least one halogen substituent, preferably chloride, attached to a titanium atom. Although the titanium halide most preferred for use is titanium tetrachloride, examples of other titanium halides which may be employed in the impregnation step include titanium tetrafluoride, titanium tetrabromide, titanium tetraiodide, titanium trichloride, as well as the mixed halides of Ti(III) or Ti(IV). In addition to halide, other substituents such as alkoxide or amino groups may also be present. Preferably, however, all the substituents attached to titanium are halide.

While the concentration of titanium halide in the hydrocarbon solvent is not critical, the titanium halide concentration will typically be in the range of from 0.01 moles/liter to 1.0 moles/liter. The concentration of the titanium halide in the hydrocarbon solvent and the amount of solution used is desirably adjusted to provide a titanium content in the final catalyst of from 0.1 to 10 percent by weight (calculated as Ti based on the total weight of the catalyst). The optimum titanium content is influenced by a number of factors. Generally speaking, the higher the surface area of the inorganic siliceous solid, the greater the amount of titanium which can be incorporated into the catalyst without loss of activity (as measured at a constant Ti level under the epoxidation conditions) or selectivity. Where the surface area of the inorganic siliceous solid is in the range of from 250 to 375 $m^2/g$, for example, the titanium content of the catalyst is desirably from 1 to 5 weight percent. Multiple impregnations, with or without intervening drying and/or calcination, may be used to achieve the desired titanium content and activity.

Suitable inorganic siliceous solids for purpose of this invention are solid materials which contain a major proportion of silica (silicon dioxide). Amorphous (i.e., non-crystalline) silicon oxides are particularly preferred for use. In general, suitable inorganic siliceous solids are further characterized by having a relatively large surface area in relation to their mass. The term used herein and one normally used in the art to express the relationship of surface area to mass is "specific surface area". Numerically, specific surface area will be expressed as square meters per gram ($m^2/g$). Generally, the inorganic siliceous solid has a specific surface area of at least 1 $m^2/g$ and preferably the average specific surface area is from 25 $m^2/g$ to 1200 $m^2/g$.

Suitable inorganic siliceous solids include synthetic porous silicas consisting of particles of amorphous silica flocculated or linked together so that they form relatively dense, close-packed masses. Representatives of such materials are silica gel and precipitated silica. These silica products are porous, in that they have numerous pores, voids, or interstices throughout their structures.

Other suitable inorganic siliceous solids include synthetic silica powders consisting of particles of amorphous silica flocculated in open-packed, readily disintegrated, loosely knit aggregates. Illustrative silica powders include fumed, pyrogenic silicas obtained by the combustion of hydrogen and oxygen with silicon tetrachloride or tetrafluoride.

Synthetic inorganic oxide materials containing a major proportion of silica comprise another class of inorganic siliceous solids. Such materials are known as refractory oxides and includes silica-alumina, silica-magnesia, silica-zirconia, silica-alumina-boric and silica-alumina-magnesia. Molecular sieves, particularly large pore or mesoporous molecular sieves such as MCM-41, MCM-48 and M41S, may also be utilized as the inorganic siliceous solid.

Particularly preferred synthetic inorganic siliceous solids are those consisting essentially of pure silica, e.g., materials containing at least 99% silica.

Siliceous inorganic solids are well-known in the art and have previously been used in the preparation of titanium-containing heterogeneous catalysts as described, for example, in U.S. Pat. Nos. 4,367,342, 4,021,454, 3,829,392 and 3,923,843, European Patent Publication Nos. 0129814, 0345856, and 0734764, Japanese Kokai No. 77-07,908 (Chem. Abstracts 98:135000s), PCT Application No. WO 94/23834, German Patent Document No. 3,205,648, and Castillo et al., *J. Catalysis* 161, pp. 524–529 (1996), the teachings of which are incorporated herein by reference in their entirety. Any of the siliceous inorganic solids described in these references are also suitable for use in the presently claimed invention.

It is highly desirable to dry the inorganic siliceous solid prior to impregnation. Drying may be accomplished, for example, by heating the inorganic siliceous solid for several hours at a temperature of 100° C. to 700° C., preferably at least 200° C. Generally speaking, there is no need to employ temperatures in excess of 700° C. in order to attain a sufficient degree of dryness. Vacuum or a flowing stream of a dry gas such as nitrogen may be applied to accelerate the drying process.

Any of the conventionally employed means of impregnating a porous solid with a soluble impregnating agent may be used. For example, the titanium halide may be dissolved in the hydrocarbon solvent and then added to or otherwise combined with the inorganic siliceous solids. The inorganic siliceous solids could also be added to the hydrocarbon solution of the titanium halide.

"Incipient wetness" impregnation techniques, whereby a minimum quantity of solvent is utilized in order to avoid formation of a slurry, are also suitable for use. The resulting mixture may be aged, optionally with agitation or other mixing, prior to further processing. Generally speaking, the impregnating solution should be placed in contact with the inorganic siliceous solids for a period of time sufficient for the solution to completely penetrate the available pore volume of the solids. The hydrocarbon solvent used for impregnation may thereafter be removed by drying at moderately elevated temperature (e.g., 50° C. to 200° C.) and/or reduced pressure (e.g., 1 mm Hg to 100 mm Hg) prior to calcination. The conditions in the solvent removal step are preferably selected so that at least 80%, more preferably at least 90%, of the hydrocarbon solvent used for impregnation is removed prior to calcination. The drying step may be preceded by decantation, filtration or centrifugation to remove any excess impregnation solution. Washing of the impregnated siliceous solid is not necessary. Thus, one desirable embodiment of this invention is characterized by the absence of such a washing step.

The impregnated siliceous solids are calcined by firing at an elevated temperature. Calcination may be performed in the presence of oxygen (from air, for example) or, more preferably, an inert gas which is substantially free of oxygen such as nitrogen, argon, neon, helium or the like or mixture thereof. The use of a substantially oxygen-free atmosphere during calcination generally yields a much more active catalyst than when an oxygen-containing atmosphere such as air is utilized. In one embodiment of the invention, calcination is first performed in a substantially oxygen-free atmosphere with oxygen being introduced thereafter. Preferably, the calcination atmosphere contains less than 10,000 ppm mole oxygen. More preferably, less than 2000 ppm mole oxygen is present in the calcination atmosphere. Ideally, the oxygen concentration during calcination is less than 500 ppm. It is recognized, however, that substantially oxygen-free conditions are difficult to attain in large scale commercial operations. It has surprisingly been found that catalysts having epoxidation activity comparable to that of catalysts calcined in the substantial absence of oxygen may be obtained even when some oxygen (e.g., up to 25,000 ppm mole) is present if a reducing gas is also present. Carbon monoxide is a particularly effective reducing gas for this purpose. The use of hydrogen as the reducing gas is generally not desirable, since the catalysts thereby obtained are lower in activity (possibly due to the formation of water under the calcination conditions). The optimum amount of the reducing gas will, of course, vary depending upon a number of factors including the oxygen concentration in the calcination atmosphere and the identity of the reducing gas, but reducing gas levels of from 0.1 to 10 mole % in the calcination atmosphere are typically sufficient. In one embodiment of the invention, calcination is performed in an atmosphere comprised of oxygen, a reducing gas (preferably carbon monoxide) and, optionally, one or more inert gases (e.g., nitrogen, helium, argon, carbon dioxide).

The catalyst may be maintained in a fixed bed during calcination with a stream of gas being passed through the catalyst bed. To enhance the epoxidation activity of the catalyst, it is important that the calcination be performed at a temperature of at least 500° C. More preferably, the calcination temperature is at least 700° C. but no greater than 1000° C. Typically, calcination times of from about 0.1 to 24 hours will be sufficient.

The catalyst may be reacted with water after and/or during calcination. Such reaction can be effected by, for example, contacting the catalyst with steam at an elevated temperature (preferably, a temperature in excess of 100° C., more preferably, a temperature in the range of 150° C. to 650° C.) for from about 0.1 to 6 hours. Reaction with water is desirable in order to reduce the amount of residual halide in the catalyst derived from the titanium halide reagent and to increase the hydroxy density of the catalyst.

The catalyst may also be treated with an organic silylating agent at elevated temperature. Epoxide selectivity is generally improved by silylation. Silylation is preferably performed after calcination and most preferably after both calcination and reaction with water. Suitable silylation methods adaptable for use in the present invention are described in U.S. Pat. Nos. 3,829,392 and 3,923,843 (incorporated hereby by reference in their entirety). Suitable silylating agents include organosilanes, organosilylamines and organosilazanes.

Organosilanes containing from one to three organic substituents may be utilized, including, for example, chlorotrimethylsilane, dichlorodimethyl silane, nitrotrimethyl-silane, chlorotriethylsilane, chlorodimethylphenylsilane and the like. Preferred organohalosilane silylating agents include tetra-substituted silanes having from 1 to 3 halo substituents selected from chlorine, bromine, and iodine with the remainder of the substituents being methyl, ethyl or a combination thereof.

Organodisilazanes are represented by the formula

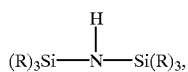

wherein the R groups are independently hydrocarbyl groups (preferably, $C_1$–$C_4$ alkyl) or hydrogen. Especially preferred for use are the hexaalkyl substituted disilazanes such as, for example, hexamethyidisilazane.

Treatment with the silylating agent may be performed either in the liquid phase (i.e., where the silylating agent is applied to the catalyst as a liquid, either by itself or as a solution in a suitable solvent such as a hydrocarbon) or in the vapor phase (i.e., where the silylating agent is contacted with the catalyst in the form of a gas). Treatment temperatures are preferably in the 80° C. to 450° C. range, with somewhat higher temperatures (e.g., 300° C. to 425° C.) being generally preferred wherein the silylating agent is an organohalosilane and somewhat lower temperatures (e.g., 80° C. to 300° C.) being preferred for the organosilazanes. The silylation may be carried out in a batch, semi-continuous, or continuous manner.

The length of time required for the silylating agent to react with the surface of the catalyst depends in part on the temperature and agent employed. Lower temperatures generally require longer reaction times. Generally, times of from 0.1 to 48 hours are suitable.

The amount of silylating agent employed can vary widely. Suitable amounts of silylating agent can range from about 1 percent by weight (based on the weight of the entire catalyst composition) to about 75 percent by weight, with amounts of from 2 to 50 percent by weight typically being preferred. The silylating agent can be applied to the catalyst either in one treatment or a series of treatments.

The catalyst composition obtained by the aforedescribed procedure will generally have a composition comprising from about 0.1 to 10 percent (preferably, 1 to 5 percent) by weight titanium (in the form of titanium oxide, typically, and preferably, in a high positive oxidation state) with the balance being, in preferred embodiments of the invention, predominately or exclusively silica (silicon dioxide). Where the catalyst has been silylated, it will typically also contain 1 to 4 percent by weight carbon in the form of organic silyl groups. Relatively minor quantities of halide (e.g., up to about 5000 ppm) may also be present in the catalyst. A desirable feature of this invention is that it is capable of producing highly active and selective catalyst compositions containing relatively large amounts of titanium (e.g., 1 weight % and higher). This advantage was completely unexpected in view of the prior art teachings that oxygen-containing solvents must be used in a liquid phase impregnation procedure in order to minimize titanium agglomeration and maximize catalyst efficiency. The catalyst is typically porous in character, has a relatively high surface area, and may be characterized as comprising an inorganic oxygen compound of silicon in chemical combination with an inorganic oxygen compound of titanium (e.g., oxide or hydroxide).

The catalyst compositions may optionally incorporate non-interfering and/or catalyst promoting substances, especially those which are chemically inert to the epoxidation reactants and products. The catalysts may contain minor amounts of promoters, for example, alkali metals (e.g., sodium, potassium) or alkaline earth metals (e.g., barium, calcium, magnesium) as oxides or hydroxides. Alkali metal and/or alkaline earth metal levels of from 0.01 to 5% by weight based on the total weight of the catalyst composition are typically suitable.

The catalyst compositions may be employed in any convenient physical form such as, for example, powder, flakes, granules, spheres or pellets. The inorganic siliceous solid may be in such form prior to impregnation and calcination or, alternatively, be converted after impregnation and/or calcination from one form to a different physical form by conventional techniques such as extrusion, pelletization, grinding or the like.

As olefinic reactant in the epoxidation process of this invention may be employed any hydrocarbon having at least one olefinically carbon-carbon double bond, and generally from 2 to 60 carbon atoms but preferably from 3 to 10 carbon atoms.

Especially preferred olefinic reactants are the acyclic alkenes of from 3 to 10 carbon atoms such as propylene, butene, pentene, hexene, heptene, octene, nonene, decene, and isomers thereof. Also preferred are olefinically unsaturated compounds substituted with a hydroxyl group or a halogen group such as allyl chloride or allyl alcohol. Preferred organic hydroperoxides are hydrocarbon hydroperoxides having from 3 to 20 carbon atoms. Particularly preferred are secondary and tertiary hydroperoxides of from 3 to 15 carbon atoms, especially secondary alkyl hydroperoxides wherein the hydroperoxy group is on a carbon atom attached directly to an aromatic ring, e.g., ethylbenzene hydroperoxide. Other exemplary organic hydroperoxides suitable for use include t-butyl hydroperoxide, t-amyl hydroperoxide, cyclohexyl hydroperoxide, and cumene hydroperoxide.

In such an epoxidation process the olefin: hydroperoxide molar ratio is not particularly critical, but it is preferable to employ a molar ratio of from 1:1 up to 20:1.

The epoxidation reaction is conducted in the liquid phase in solvents or diluents which are liquid at the reaction temperature and pressure and are substantially inert to the reactants and the products produced therefrom. In commercial practice, it will generally be most economical to use as a solvent the hydrocarbon used to produce the organic hydroperoxide reactant. For example, when ethylbenzene hydroperoxide is utilized, the use of ethylbenzene as the epoxidation solvent is preferred. It is conducted at moderate temperatures and pressures. Typically, the organic hydroperoxide is present at concentrations of from about 1 to 50 percent by weight of the epoxidation reaction mixture (including olefin). Suitable reaction temperatures vary from 0° C. to 200° C., but preferably from 25° C. to 150° C. The reaction is preferably conducted at or above atmospheric pressure. The precise pressure is not critical. The reaction mixture may, for example, be maintained substantially in a non-gaseous phase or as a two phase (gas/liquid) system. The catalyst composition, of course, is heterogeneous in character and thus is present as a solid phase during the epoxidation process of this invention. Typical pressures vary from 1 atmosphere to 100 atmospheres.

The epoxidation may be performed using any of the conventional reactor configurations known in the art for reacting olefin and organic hydroperoxide in the presence of an insoluble catalyst. Continuous as well as batch procedures may be used. For example, the catalyst may be deployed in the form of a fixed bed or slurry with provisions being made for removal of heat generated as a result of the exothermic epoxidation reaction. A fixed bed catalytic reactor adaptable for use with the present process is described in EP 323,663. When the epoxidation has proceeded to the desired extent, the product mixture is separated and the products (epoxide and the alcohol derived from the organic hydroperoxide) recovered by conventional methods such as fractional distillation, selective extraction, filtration, and the like. The reaction solvent, the catalyst composition, and any unreacted olefin or organic hydroperoxide are recycled for further utilization.

EXAMPLES

Example 1-A

This example demonstrates the preparation of a catalyst in accordance with the invention.

A dried sample of Grace V-432 silica (30 g) having a surface area of 320 m$^2$/g and a pore volume of 1.1 mL/g was charged to a 500 mL 3-neck round bottom flask equipped with a condenser, inert gas inlet, and a scrubber containing an aqueous solution of sodium carbonate. A solution containing 51 g heptane and 2.1 mL (3.6 g; 0.019 mol) titanium tetrachloride was then added to the flask under a dry inert gas atmosphere. The resulting mixture was heated to reflux for 2 hours using an oil bath. The temperature of the oil bath was then increased to 150° C. and solvent driven off by passing an inert gas through the flask. The oil bath temperature was increased to 200° C. and maintained at that temperature for 2 hours.

The resulting solids were charged into a quartz reactor and heated to 800° C. under a flowing air stream. The hydrochloric acid generated while the temperature was being increased was scrubbed using the aqueous sodium carbonate solution. The product was then calcined in the presence of the flowing air stream at 800° C. for 2 hours. The quartz reactor was cooled to 400° C. and its contents treated with steam at that temperature using an inert gas as a carrier. A total of 4.5 g (0.25 mol) water was passed through the bed of catalyst. After cooling the quartz reactor to 200° C., the catalyst was treated with a flowing stream of inert gas containing hexamethyidisilazane in vapor form. A total of 3.0 g of hexamethyldisilazane was passed through the catalyst. The reactor was thereafter cooled to ambient temperature under inert gas flow to yield the final catalyst composition.

Example 1-B

The procedure of Example 1-A was repeated except that the steaming was performed at 500° C. using air as the carrier gas.

Example 1-C

The procedure of Example 1-A was repeated except that the steaming was performed at 600° C. using air as the carrier gas.

Example 1-D

The procedure of Example 1-A was repeated except that the catalyst was calcined at 600° C.

Example 1-E

The procedure of Example 1-A was repeated except that the catalyst was calcined at 700° C.

Example 1-F

The procedure of Example 1-A was repeated except that the catalyst was calcined at 900° C.

Example 1-G

The procedure of Example 1-A was repeated except that the steaming treatment was omitted.

Example 1-H

The procedure of Example 1-A was repeated except that the silylation step was omitted.

Example 1-I (Comparative)

The procedure of Example 1-A was repeated except that anhydrous isopropanol was used as the solvent for impregnation instead of heptane.

Comparative Example 2

This example demonstrates, for comparative purposes, the preparation of a catalyst using an alcohol as an impregnation solvent and a titanium alkoxide as a source of titanium.

A solution containing 137 g isopropanol and 13.8 g titanium diisoproproxide bis (acetyl acetonate) is prepared.

The solution is added to dried silica (the relative amounts being varied to provide Catalyst 2-A and Catalyst 2-B, which have different titanium contents, as shown in Table I) in a round bottom flask and mixed well. The solvent is thereafter removed using a rotary evaporator having a bath temperature of 85° C. After drying, the material is calcined at 800° C. (5° C./min ramp rate) in air for 6 hours.

A portion of the calcined product (78 g) is charged into a tubular glass reactor (1.25 in. O.D.; 30 in. long) equipped with a thermowell, 500 mL 3-neck round bottom flask, heating mantle, inert gas inlet, and a scrubber containing water. The reactor is heated using a 3-zone furnace under nitrogen flow (300–600 cc/min.). The power outputs are adjusted so that the temperature in each of the three zones is between 190° C. and 200° C. Hexamethyldisilazane (5.7 g) is added to the flask and the flask then heated to reflux using the heating mantle. Vapors of the hexamethyidisilazane are carried through the catalyst bed using inert gas. After 1 hour, all the hexamethyl-silazane is consumed. The bed temperature is maintained at 190° C.–200° C. while continuing to pass a stream of inert gas through the reactor bed for 5 hours. The apparatus is then cooled to ambient temperature under an inert gas flow.

Example 3

To evaluate the performance of the catalysts prepared in Example 1 and Comparative Example 2, batch epoxidations of 1-octene using ethylbenzene hydroperoxide were carried out. The following procedure was employed: A mixture containing 17.0 g 1-octene, 10 g of a solution of ethylbenzene hydroperoxide in ethyl-benzene (obtained by air oxidation of ethyl benzene), and 1.0 g nonane (internal standard) is charged to a 4-neck round bottom flask equipped with a condenser, thermocouple, stirrer bar and a sampling port. The catalyst (0.5 g) is added after heating the mixture to 80° C. The mixture is maintained at 80° C. for 30 minutes.

The batch epoxidation results obtained using the catalysts prepared as described hereinabove are summarized in Table I. Conversion and selectivity are calculated based on gas chromatographic analysis of the feed and reaction product.

These results show that, at similar titanium loadings, catalyst prepared using liquid phase impregnation of silica with a solution of titanium tetrachloride in a hydrocarbon is higher in both activity and selectivity than catalyst prepared using liquid phase impregnation of silica with a solution of a titanium alkoxide in an alcohol.

TABLE 1

| Catalyst | Titanium wt. % | Conversion (%) | Epoxide Selectivity (%) |
|---|---|---|---|
| 1-A | 2.8 | 85 | 85 |
| 1-B | 2.9 | 80 | 84.6 |
| 1-C | 2.9 | 85 | 84.5 |
| 1-D | 2.9 | 72 | 86 |
| 1-E | 2.63 | 68 | 82.5 |
| 1-F | 2.8 | 80 | 84.6 |
| 1-G | 3.0 | 74 | 83 |
| 1-H | 3.1 | 74 | 78 |
| 1-I* | 3.0 | 34 | 86 |
| 2-A* | 0.97 | 60 | 87 |
| 2-B* | 2.66 | 63 | 81 |

*comparative example

Example 4-A

A dried sample of silica (30 g) was charged into a 500 mL 3-neck round bottom flask equipped with a condenser, inert gas inlet and a scrubber containing sodium carbonate solution. A solution containing 51 g heptane and 2.1 mL (3.6 g; 0.019 mol) $TiCl_4$ was then added to the flask under a dry inert gas atmosphere. After thoroughly mixing the contents of the flask, the oil bath temperature was raised to 150° C. and solvent driven off by flowing inert gas through the system. The oil bath temperature was then further increased to 200° C. and maintained at that temperature for 2 hours. The dried impregnated silica was then charged to a quartz reactor and heated to 850° C. with a stream of air being passed through the reactor. The HCl produced while the temperature was being increased was scrubbed using the sodium carbonate solution. After continuing to heat at 850° C. for 0.5 hours, the reactor was cooled to 400° C. and the catalyst treated with steam using an inert gas as the carrier gas. A total of 4.5 g (0.25 mol) water was passed through the catalyst bed. The reactor was thereafter cooled to 200° C. and the catalyst then treated with a stream of flowing inert gas containing hexamethyl-disilazane (HMDS) in vapor form. A total of 3.0 g HMDS was passed through the catalyst bed. The reactor was then cooled down under a flowing stream of inert gas.

Example 4-B

Example 4-A was repeated, except that the calcination was performed at 850° C. for 30 minutes using a flowing helium stream.

Example 4-C

Example 4-A was repeated, except that the calcination was performed using a flowing helium stream and the temperature during calcination was raised to 900° C. and then lowered to 600° C. in a 1.5 hour period.

Example 4-D

Example 4-A was repeated, except that the hexane was used as the impregnation solvent.

Example 5

The catalytic performance of the materials prepared in Examples 4-A through 4-D was compared using the same batch epoxidation procedure described in Example 3. The results obtained, which are summarized in the following Table II, confirm that activity is enhanced significantly when calcination is performed under an inert atmosphere (Examples 4-B through 4-D) instead of an oxygen-containing atmosphere (Example 4-A). No detrimental effect on epoxide selectivity is observed.

TABLE II

| Catalyst | Titanium, wt. % | Conversion, % | Epoxide Selectivity, % |
|---|---|---|---|
| 4-A | 3.25 | 80 | 85 |
| 4-B | 3.1 | 90 | 85.6 |
| 4-C | 3.2 | 91 | 86.5 |
| 4-D | 2.8 | 90 | 86 |

Example 6

The performance of Catalyst 4-A was tested in a fixed-bed propylene epoxidation reaction. The reactor was loaded with 25 g of catalyst. A reaction mixture of 12 mol of propylene per mol of ethylbenzene hydroperoxide in ethylbenzene was fed to the reactor at a liquid hourly space velocity of 8 $hr^{-1}$ and a pressure of 885 psig. The concentration of ethylbenzene hydroperoxide in ethylbenzene was 35 wt. %. After 266 hours, the average bed temperature was 78° C., and ethylbenzene hydroperoxide conversion and propylene oxide selectivity were 98% and 99% respectively.

Example 7

The performance of catalyst 4-C was tested under the same conditions as in Example 6. After 261 hours, the average bed temperature was 73° C., and ethylbenzene hydroperoxide conversion and propylene oxide selectivity were 99% and 98% respectively.

Example 8-A

A dried sample of silica (103 g) was charged into a 500 mL 3-neck round bottom flask equipped with an inert gas inlet, a gas outlet, and a scrubber containing aqueous sodium hydroxide solution. A solution containing 143 g n-heptane (99+%; <50 ppm water) and 7.4 mL titanium (IV) tetrachloride (12.8 g; 0.067 mol) was added to the flask under a dry inert gas atmosphere. The mixture was mixed well by swirling. Solvent was removed using a rotary evaporator at 80° C. and 5–10 mbar pressure.

A portion of the dried impregnated silica thereby obtained was charged into a tubular quartz reactor (1 inch ID, 16 in long) equipped with a thermowell, a 500 mL 3-neck round bottom flask, a heating mantle, an inert gas inlet and a scrubber (containing aqueous sodium hydroxide). The bed of impregnated silica was heated to 850° C. under dry nitrogen (99.999% purity) flow (400 cc/min). After the bed temperature had been at 850° C. for 30 minutes, the power to the furnace was turned off and the catalyst bed cooled down to 400° C.

Water (5.0 g) was then added to the 3-neck round bottom flask and the contents of the flask heated with a heating mantle to reflux while maintaining a $N_2$ flow of 400 cc/min. The water was distilled through the catalyst bed over a period of 30 minutes, with a heat gun being used to heat the round-bottom flask to ensure that all residual water had been driven out of the flask and through the catalyst bed. After maintaining the bed at 400° C. for an additional 2 hours, the tube reactor was permitted to cool to room temperature.

The steam-treated catalyst thereby obtained (35 g) was charged to a 500 mL 3-neck round bottom flask, together with 70 g heptane (<50 ppm water) and 4.4 g hexamethyl disilazane. The flask was equipped with a condenser, thermometer and inert gas inlet. The flask was then heated using a 115° C. oil bath to reflux (98° C.) under an inert atmosphere and kept at reflux for 4 hours. After cooling down under an inert gas atmosphere, the catalyst composition was collected by filtration, washed with 100 mL heptane, and then dried in a flask under a flow of inert gas at 180 to 200° C. for 2 hours.

Example 8-B

A catalyst composition was prepared using the same procedure described in Example 8-A except that the calcination and steaming steps were performed under air flow instead of nitrogen.

Example 8-C

A catalyst composition was prepared using the same procedure described in Example 8-A except that the calcination and steaming steps were performed using nitrogen containing 2000 ppm mole oxygen.

Example 8-D

A catalyst composition was prepared using the same procedure described in Example 8-A except that the calcination and steaming steps were performed using nitrogen containing 4 mole % carbon monoxide.

Example 8-E

A catalyst composition was prepared using the same procedure described in Example 8-A except that the calcination and steaming steps were performed using nitrogen containing 6000 ppm mole oxygen and 4 mole % carbon monoxide.

Example 8-F

A catalyst composition was prepared using the same procedure described in Example 8-A except that the calcination and steaming steps were performed using nitrogen containing 1 mole % hydrogen.

Example 8-G

A catalyst composition was prepared using the same procedure described in Example 8-A except that the calcination and steaming steps were performed using nitrogen containing 4 mole % hydrogen and 0.5 mole % oxygen.

Example 8-H

A catalyst composition was prepared using the same procedure described in Example 8-A except that the calcination was performed at 500° C. for 30 minutes.

Example 8-I

A catalyst composition was prepared using the same procedure described in Example 8-A except that the calcination was performed at 400° C. for 30 minutes.

Example 8-J

A catalyst composition was prepared using the same procedure described in Example 8-A except that the calcination was performed at 300° C. for 30 minutes.

Example 9

The catalyst compositions prepared in Examples 8-A through 8-J were tested in a batch epoxidation of 1-octene using the following procedure. A feed solution is prepared by mixing 170 g 1-octene, 100 g ethyl benzene hydroperoxide solution in ethyl benzene (prepared by air oxidation of ethyl benzene) and 10 g nonane (internal standard). A 3-neck 100 mL round bottom flask equipped with a condenser, thermocouple, stirrer bar, and sampling port is immersed in a 60° C. oil bath under an inert atmosphere and then charged with a 28 g portion of the aforementioned feed solution. The feed solution in the flask is warmed to 58–59° C. while the stirrer bar is stirred at a rate of 700 rpm. A 0.5 g portion of the catalyst composition to be tested is then added to the flask. The temperature of the reaction mixture is monitored at 1 minute intervals for the first 10 minutes, then at 5 minute intervals. The reaction mixture temperature generally fluctuates between 60 and 63° C. A 3 mL sample of the reaction mixture is taken 30 minutes after addition of the catalyst composition. Both the feed solution and the product samples are analyzed by gas chromatography to determine the hydroperoxide and epoxy octane concentrations. Conversion and epoxide selectivity relative to hydroperoxide consumed are calculated.

The epoxidation results obtained are shown in Table III. The composition of the atmosphere under which calcination is performed was found to significantly affect the catalyst activity. Even the small amount of oxygen present during calcination in Example 8-C results in the production of a less active catalyst (Compare Run 9-C with Run 9-A). However the detrimental effect of low levels of oxygen can be avoided by having a reducing gas such as carbon monoxide also present during calcination (see Run 9-E). Calcination temperature was found to be another important factor affecting the activity of the catalyst. When this temperature was reduced from 850° C. to 500° C., the conversion of ethylbenzene hydroperoxide dropped by more than half (compare Run 9-A and Run 9-H). Further losses in catalyst activity were observed as the calcination temperature was decreased below 500° C.

TABLE III

| Run | Catalyst | EBHP Conversion, % | Epoxide Selectivity, % |
|---|---|---|---|
| 9-A | Example 8-A | 69 | 89 |
| 9-B | Example 8-B | 48 | 86 |
| 9-C | Example 8-C | 53 | 88 |
| 9-D | Example 8-D | 67 | 88 |
| 9-E | Example 8-E | 68 | 88 |
| 9-F | Example 8-F | 61 | 87 |
| 9-G | Example 8-G | 40 | 89 |
| 9-H | Example 8-H | 33 | 90 |
| 9-I | Example 8-I | 25 | 88 |
| 9-J | Example 8-J | 24 | 87 |

We claim:

1. An epoxidation process comprising contacting an organic hydroperoxide with an olefin in the presence of a catalyst composition obtained by a method comprising the steps of:
   (a) impregnating an inorganic siliceous solid with a solution consisting essentially of a titanium halide in a non-oxygenated hydrocarbon solvent; and
   (b) calcining the impregnated siliceous solid to form the catalyst composition;
   said method being wherein the substantial exclusion of water until at least after step (a) is completed.

2. The epoxidation process of claim 1 wherein the titanium halide is titanium tetrachloride.

3. The epoxidation process of claim 1 wherein impregnation step (a) is accomplished by combining a solution of the titanium halide in the non-oxygenated hydrocarbon solvent with the inorganic siliceous solid and thereafter removing the hydrocarbon solvent.

4. The epoxidation process of claim 1 wherein the inorganic siliceous solid is silica.

5. The epoxidation process of claim 1 wherein the non-oxygenated hydrocarbon solvent is selected from the group consisting of $C_5$–$C_{12}$ aliphatic hydrocarbons, $C_6$–$C_{12}$ aromatic hydrocarbons, $C_1$–$C_{10}$ halogenated aliphatic hydrocarbons, $C_6$–$C_{10}$ halogenated aromatic hydrocarbons, and mixtures thereof.

6. The epoxidation process of claim 1 wherein the method of obtaining the catalyst composition comprises an additional step after step (b) of heating the catalyst composition in the presence of water.

7. The epoxidation process of claim 1 wherein water is substantially excluded until after step (b) is completed.

8. The epoxidation process of claim 1 wherein the method of obtaining the catalyst composition comprises an additional step after step (b) of treating the catalyst composition with a silylating agent.

9. The epoxidation process of claim 1 wherein the method of obtaining the catalyst composition comprises additional steps after step (b) of heating the catalyst composition in the presence of water and treating the catalyst composition with a silylating agent.

10. The epoxidation process of claim 1 wherein calcination step (b) is performed at a temperature of at least 500° C.

11. The epoxidation process of claim 1 wherein the organic hydroperoxide is ethylbenzene hydroperoxide.

12. The epoxidation process of claim 1 wherein the olefin is a $C_3$–$C_{10}$ acyclic alkene.

13. The epoxidation process of claim 1 wherein step (b) is performed in a substantially oxygen-free atmosphere.

14. The epoxidation process of claim 1 wherein step (b) is performed in an atmosphere comprised of oxygen and a reducing gas.

15. An epoxidation process comprising contacting ethylbenzene hydroperoxide with propylene in the presence of a catalytically effective amount of a catalyst composition obtained by a method comprising the steps of:
  (a) forming a mixture by combining a solution consisting essentially of titanium tetrachloride in a hydrocarbon solvent selected from the group consisting of $C_5$–$C_{12}$ aliphatic hydrocarbons, $C_6$–$C_{12}$ aromatic hydrocarbons, $C_1$–$C_{10}$ halogenated aliphatic hydrocarbons, $C_6$–$C_{10}$ halogenated aromatic hydrocarbons, and mixtures thereof with silica;
  (b) removing the hydrocarbon solvent from the mixture to yield an impregnated silica;
  (c) calcining the impregnated silica at a temperature of from 700° C. to 1000° C. to form a calcined catalyst precursor;
  (d) heating the calcined catalyst precursor in the presence of water; and
  (e) treating the calcined catalyst precursor with a silylating agent;
said method being wherein the substantial exclusion of water until after step (c) is completed.

16. The epoxidation process of claim 15 wherein step (c) is performed in a substantially oxygen-free atmosphere.

17. The epoxidation process of claim 15 wherein step (c) is performed in an atmosphere comprised of oxygen and a reducing gas.

18. The epoxidation process of claim 15 wherein the silylating agent is selected from the group consisting of organosilanes, organosilylamines, organosilazanes, and mixtures thereof.

19. The epoxidation process of claim 15 wherein the catalyst composition has a Ti content of from 1 to 5 weight percent.

20. The epoxidation process of claim 15 wherein the method of obtaining the catalyst composition comprises the additional step prior to step (a) of drying the silica.

21. A method for preparing a catalyst composition comprising the steps of:
  (a) impregnating an inorganic siliceous solid with a solution consisting essentially of a titanium halide in a non-oxygenated hydrocarbon solvent;
  (b) calcining the impregnated siliceous solid to form a calcined catalyst precursor; and at least one of steps (c) or (d);
  (c) heating the calcined catalyst precursor in the presence of water; or
  (d) treating the calcined catalyst precursor with a silylating agent;
said method being wherein the substantial exclusion of water until at least after step (a) is completed.

22. The method of claim 21 wherein step (b) is performed in a substantially oxygen-free atmosphere.

23. The method of claim 21 wherein the titanium halide is titanium tetrachloride.

24. The method of claim 21 wherein impregnation step (a) is accomplished by combining a solution of the titanium halide in the non-oxygenated hydrocarbon solvent with the inorganic siliceous solid and thereafter removing the hydrocarbon solvent.

25. The method of claim 21 wherein the inorganic siliceous solid is silica.

26. The method of claim 21 wherein both steps (c) and (d) are performed.

27. The method of claim 21 wherein step (b) is performed in the substantial absence of water.

28. The method of claim 21 wherein step (b) is performed in an atmosphere comprised of oxygen and a reducing gas.

29. The method of claim 21 wherein step (b) is performed at a temperature of at least 500° C.

30. A method for preparing a catalyst composition comprising the steps of
  (a) forming a mixture by combining a solution consisting essentially of titanium tetrachloride in a hydrocarbon solvent selected from the group consisting of $C_5$–$C_{16}$ aliphatic hydrocarbons, $C_5$–$C_{12}$ aromatic hydrocarbons, $C_1$–$C_{10}$ halogenated aliphatic hydrocarbons, $C_6$–$C_{10}$ halogenated aromatic hydrocarbons and mixtures thereof with silica;
  (b) removing the hydrocarbon solvent from the mixture to yield an impregnated silica;
  (c) calcining the impregnated silica at a temperature of from 700° C. to 1000° C. to form a calcined catalyst precursor;
  (d) heating the calcined catalyst precursor in the presence of water; and
  (e) treating the calcined catalyst precursor with a silylating agent;
said method being wherein the substantial exclusion of water until after step (c) is completed.

31. The method of claim 30 wherein step (c) is performed in a substantially oxygen-free atmosphere.

32. The method of claim 30 wherein step (c) is performed in an atmosphere comprised of oxygen and a reducing gas.

33. The method of claim 30 wherein the reducing gas is carbon monoxide.

34. The method of claim 30 comprising an additional step prior to step (a) of drying the silica.

* * * * *